(12) United States Patent
Mandpe

(10) Patent No.: US 9,782,297 B2
(45) Date of Patent: *Oct. 10, 2017

(54) EUSTACHIAN TUBE STENTS, INTRODUCERS AND METHODS FOR THEIR USE

(76) Inventor: Aditi H. Mandpe, San Francisco, CA (US)

(*) Notice: Subject to any disclaimer, the term of this patent is extended or adjusted under 35 U.S.C. 154(b) by 590 days.

This patent is subject to a terminal disclaimer.

(21) Appl. No.: 13/490,280

(22) Filed: Jun. 6, 2012

(65) Prior Publication Data

US 2012/0245593 A1    Sep. 27, 2012

Related U.S. Application Data

(60) Continuation-in-part of application No. 13/077,120, filed on Mar. 31, 2011, now Pat. No. 9,603,745, and a continuation-in-part of application No. 12/901,932, filed on Oct. 11, 2010, now Pat. No. 8,197,552, which is a division of application No. 11/678,919, filed on Feb. 26, 2007, now Pat. No. 7,833,282.

(60) Provisional application No. 60/767,020, filed on Feb. 27, 2006.

(51) Int. Cl.
*A61F 11/00* (2006.01)
*A61F 2/94* (2013.01)

(52) U.S. Cl.
CPC .............. *A61F 11/002* (2013.01); *A61F 2/94* (2013.01)

(58) Field of Classification Search
CPC ...... A61F 2/18; A61F 2002/183; A61F 11/00; A61F 11/002; A61F 11/004; A61F 11/006; A61F 11/008; A61F 11/06; A61F 11/12; A61F 2/94
USPC .......... 623/10, 23.64, 23.7; 604/8–10, 93.01, 604/264, 514, 540–543, 890.1, 891.1, 604/892.1; 606/108, 109
See application file for complete search history.

(56) References Cited

U.S. PATENT DOCUMENTS

| | | | |
|---|---|---|---|
| 3,530,860 A * | 9/1970 | Majoros | 606/109 |
| 6,578,581 B1 * | 6/2003 | Khalsa | 128/898 |
| 6,589,286 B1 * | 7/2003 | Litner | 623/23.7 |
| 2008/0294255 A1 * | 11/2008 | Gonzales | A61F 2/04 623/10 |

OTHER PUBLICATIONS

MicroMark. http://www.micromark.com/metal-forming-pliers-set-of-4,7068.html. Accessed Dec. 9, 2014.*

(Continued)

*Primary Examiner* — Christopher D Prone
*Assistant Examiner* — Rokhaya Diop
(74) *Attorney, Agent, or Firm* — Louis Wu

(57) ABSTRACT

A kit is provided comprising a stent, an introducer and a bender. The stent is constructed for insertion into a Eustachian tube of a human. The stent includes a member having a preinsertion form that includes opposing exterior surfaces, means for immobilizing the stent within the Eustachian tube, and means for providing fluid communication between the opposing surfaces to effect pressure equilibration therebetween. The introducer includes a guide, an engager, and a sliding mechanism. A Eustachian tube method is also provided. The method involves using the above-described kit.

24 Claims, 6 Drawing Sheets

(56) References Cited

OTHER PUBLICATIONS

MicroMark (http://www.micromark.com/metal-forming-pliers-set-of-4,7068.html) (accessed May 30, 2015).*
Micro_Mark_NPL_WayBackMachine_dated May 26, 2009 (accessed May 30, 2015.).*

* cited by examiner

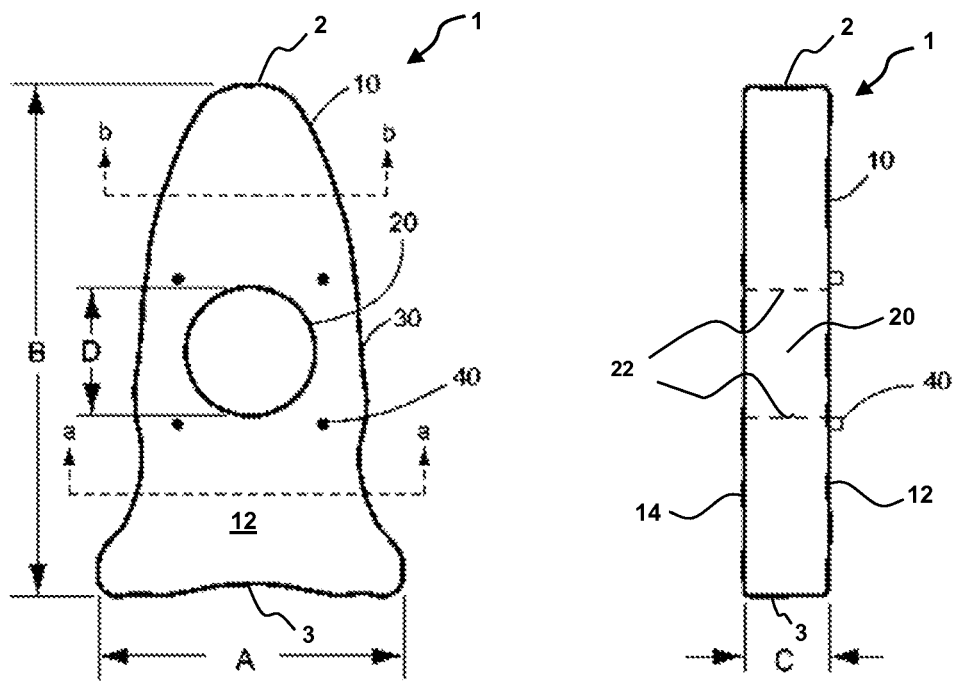
FIG. 1
FIG. 2
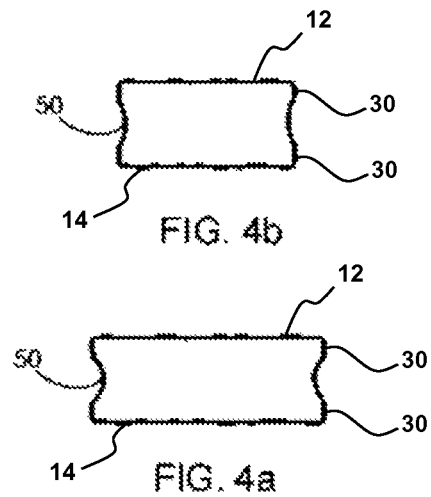
FIG. 4b
FIG. 4a
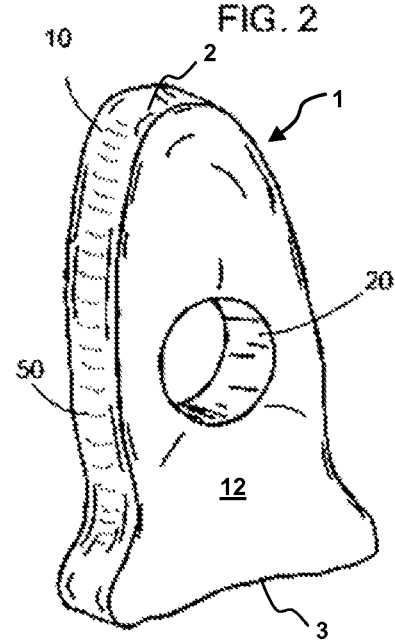
FIG. 3

EUSTACHIAN TUBE STENTS, INTRODUCERS AND METHODS FOR THEIR USE

CROSS REFERENCE TO RELATED APPLICATIONS

This application is a continuation-in-part of U.S. patent application Ser. No. 13/077,120, entitled "Introducer for Otolaryngological Devices," filed on Mar. 31, 2011, now U.S. Pat. No. 9,603,745 and a continuation-in-part of U.S. patent application Ser. No. 12/901,932, entitled "Eustachian Tube Device and Method, filed on Oct. 11, 2010, now U.S. Pat. No. 8,197,552 now allowed, which is a divisional of U.S. patent application Ser. No. 11/678,919, entitled "Eustachian Tube Device and Method," filed on Feb. 26, 2007, issued as U.S. Pat. No. 7,833,282, which claims priority to U.S. Provisional Patent Application Ser. No. 60/767,020, entitled "Eustachian Tube Dilator and Stent," filed on Feb. 27, 2006, all by inventor Aditi H. Mandpe, the disclosures of which are incorporated by reference in their entireties.

BACKGROUND

The invention generally relates to a combination of otolaryngological devices and introducers for positioning such devices within a patient's otolaryngological cavity. In particular, the invention relates to kits and methods that use introducers to engage stents through frictional forces and that position and release such stents in Eustachian tubes to render the tubes patent.

Otolaryngology is a branch of medicine and surgery that specializes in the diagnosis and treatment of ear, nose, throat, and head and neck disorders. Otolaryngologists are trained to provide comprehensive medical and surgical care for patients with diseases and disorders that affect the ears, nose, throat, the respiratory and upper alimentary systems, and related structures of the head and neck. For example, an otolaryngologist may provide expertise in head and neck oncology, facial plastic and reconstructive surgery, otology, rhinology, and laryngology. Other recognized otolaryngological subspecialities include, for example, neurotology, pediatric otolaryngology, and sleep medicine.

Numerous techniques and devices have been developed to treat various otolaryngological conditions and to help improve bodily function. For example, sinusitis, i.e., inflammation or infection of the paranasal sinuses, may be treated in a number of ways. Typically, initial treatment involves using anti-inflammatory agents to reduce the inflammation. Often, the infection is due to a bacterial source, and antibiotics are added. When unresponsive to drug therapy, chronic sinusitis may require endoscopic surgery. Under visualization through the endoscope, the surgeon may remove tissue to provide sufficient patency of sinus passageways to allow for their drainage. In addition to endoscopes, such surgery may involve the use of known devices e.g., cutting debriders, tubular guides, catheters, etc.

Recently, a number of patents have described surgical procedures involving the use of medical devices having balloon catheters. For example, patents relating to surgeries and other sinus treatments involving balloon dilation include, e.g., U.S. Pat. Nos. 7,803,150, 7,771,409, 7,753,930, 7,753,929, 7,740,642, 7,727,226, 7,727,186, 7,720,521, 7,717,933, 7,654,997, 7,648,367, 7,645,272, 7,559,925, 7,500,971, and 7,462,175. These patents generally describe flexible inflatable pressure devices that may be inserted and inflated within the sinuses. Although the devices may be navigated through the complex anatomy of the sinuses and the procedures for deploying such devices are described as minimally invasive, the devices are generally complex in construction.

In contrast, stents are often simpler in construction than their inserters. For example, U.S. Pat. No. 5,246,455 to Shikani describes a hole-type stent in the form of middle meatal antrostomy ventilation tube for use following endoscopic surgery. The tube consists of a pair of flanges and a central tubular vent section extending therebetween. The flanges are positioned perpendicular to the lumen of the central tubular vent section and serve to immobilize the tube within the antrostomy.

In addition, stents may be used for other otolaryngological procedures. For example, lumen-type stents may be used to treat chronic otitis media, which occurs when the Eustachian tube fails to ventilate the middle ear over an extended period. In these cases, fluid and thickened mucosa accumulate in the middle ear, causing hearing loss. Treatment of complications from Eustachian tube dysfunction, such as chronic otitis media may involve ventilation of the middle ear by incising the eardrum or tympanic membrane. Alternatively, as described in U.S. Pat. No. 6,589,286 to Litner, an elongate Eustachian tube stent that may be used concomitantly with middle ear surgery.

More recently, U.S. Pat. No. 7,833,282 to Mandpe describes Eustachian tube devices for insertion into a Eustachian tube without need for surgical incisions. The devices are generally considered a lumen-type stent and may include an insertable member, an immobilizing means and a fluid-communication providing means. Also provided are kits that include the device and methods for inserting the device into a Eustachian tube. Such kits may include endoscopic or other insertors for use with the Eustachian tube devices.

Nevertheless, opportunities exist to overcome disadvantages associated with known otolaryngological technologies. Specifically, opportunities exist in the art for a combination of improved introducers and Eustachian tube devices, the combination having a simple yet effective construction that allows for manipulating and positioning otolaryngological devices such as stents during medical and/or surgical procedures.

SUMMARY

In a first embodiment, a kit is provided comprising a stent, an introducer and a bender. The stent is constructed for insertion into a Eustachian tube of a human. The stent comprises a member having a preinsertion form that includes opposing exterior surfaces, means for immobilizing the stent within the Eustachian tube, and means for providing fluid communication between the opposing surfaces to effect pressure equilibration therebetween. At least one opposing surface defines a member length and member width. The opposing surfaces define a member thickness such that the member length is greater than the member thickness. The introducer includes a guide, an engager, and a sliding mechanism. The engager is slidably coupled to the guide and constructed for engaging the stent such that frictional forces, unless overcome, immobilizes the stent relative to the engager. The mechanism is constructed to slide the engager relative to the guide and to overcome the frictional forces to position and release the stent within the Eustachian tube while the member remains in the preinsertion form. The bender is effective to shape the guide of the introducer.

In another embodiment, a Eustachian tube method is provided. The method involves bending the introducer as needed to reach the Eustachian tube, and loading the above-described stent is onto the above-described introducer such that the stent is frictionally immobilized relative to the engager. Then, the introducer is manipulated to position the loaded stent in a Eustachian tube of a human. Once the stent is in proper position, the sliding mechanism is actuated in a manner to overcome the frictional forces immobilizing the stent relative to the engager. As a result, the stent is within the Eustachian tube while the member remains in the preinsertion form. The introducer is then withdrawn.

BRIEF DESCRIPTION OF THE DRAWINGS

FIG. 1 depicts in front view an exemplary device in the form of a Eustachian tube dilator stent that may be used with the inventive introducer.

FIG. 2 depicts in side view the device shown in FIG. 1.

FIG. 3 shows in perspective view of the device shown in FIG. 1.

FIGS. 4a and 4b, collectively referred to as FIG. 4, show cross sectional views near the bottom and top, respectively, of the device shown in FIG. 1.

FIG. 7a shows how the device may be loaded onto the introducer. FIG. 7b shows how the release mechanism may be actuated to unload the device from the introducer.

FIG. 8a shows how the device may be loaded onto the introducer. FIG. 8b shows how the release mechanism may be actuated to unload the device from the introducer.

FIG. 9a shows a side of the bender that contains a groove in which the guide of the introducer shown in FIG. 6 may be inserted. FIG. 9b shows in cross sectional view (along dotted line a-a) of the bender having the guide inserted into the groove thereof.

DETAILED DESCRIPTION OF THE INVENTION

Definitions and Overview

Figure 5:
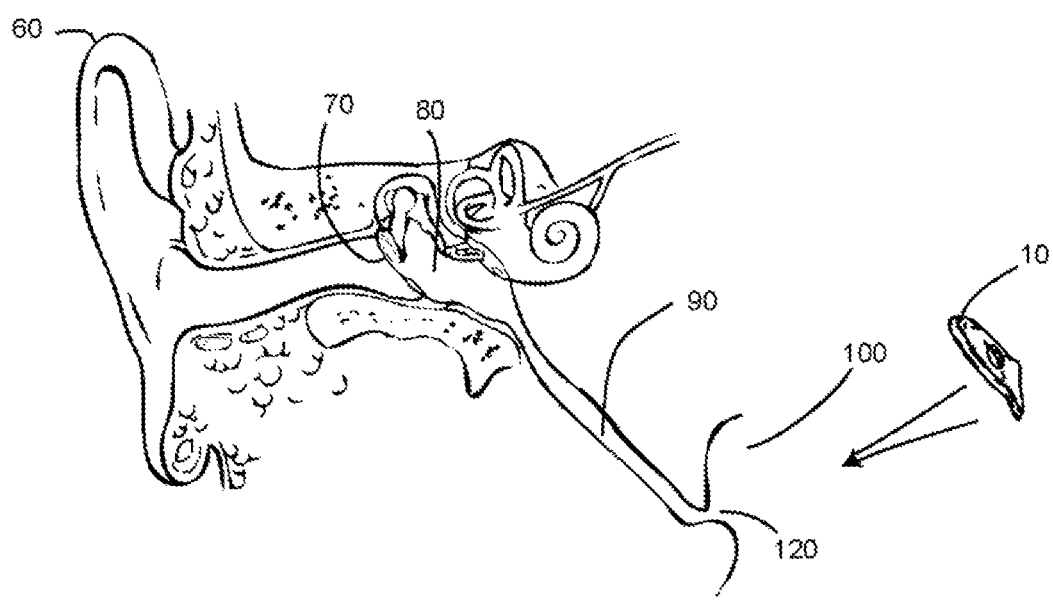
FIG. 5 depicts the placement of the device of FIG. 1 in position in the Eustachian tube at the torus tubarius.

Before describing the present invention in detail, it is to be understood that the invention is not limited to devices and methods for treatment any specific otolaryngological disorders, as such may vary. It is also to be understood that the terminology used herein is for the purpose of describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "a device" includes a single device as well as a plurality of devices, reference to "a hole" includes a plurality of holes as well as a single hole, and reference to "a surface" includes a unitary surface as well as a combination of surfaces, and the like.

In this specification and in the claims that follow, reference will be made to a number of terms that shall be defined to have the following meanings, unless the context in which they are employed clearly indicates otherwise:

"Optional" or "optionally" means that the subsequently described circumstance may or may not occur, so that the description includes instances where the circumstance occurs and instances where it does not.

The terms "otolaryngology" and "otolaryngological" are used in their ordinary sense and refer to a branch of medicine that deals with diagnosis and treatment of diseases of the ear, nose, and throat. The terms also encompass head and neck surgery. The terms are used synonymously used herein with the acronym "ENT" for "ear, nose and throat."

The terms "substantial" and "substantially" are referred to herein in their ordinary sense and are used to describe matters that are, e.g., considerable in importance, value, degree, amount, and/or extent. For example, adjacent surfaces that are "substantially perpendicular" to each other should generally define planes that intercept each other at an angle of approximately 90°, but an interception angle of precisely 90° is not required. Other uses of the term "substantially" involve an analogous definition.

In general, then, the invention pertains to an introducer in combination with an otolaryngological device. The introducer includes a guide, a stopper, an engager, and a release mechanism. The stopper is positioned closer to a distal than a proximal portion of the guide, and the engager is movably coupled to the guide. The release mechanism is attached to the engager and positioned closer to the proximal portion of the guide than the stopper. Optionally, the release mechanism is closer to the proximal portion than the distal portion of the guide.

The introducer is used in combination with an otolaryngological device, e.g., that has a first surface and a second surface that is nonparallel to the first surface. A device may be loaded on the introducer by frictionally engaging the first surface of the device to a distal terminus of the engager. Once the introducer has been used to position the device in place, the release mechanism may be actuated to unload the device from the introducer. Upon actuation, the release mechanism slides the distal terminus of the engager toward the guide while the stopper abuts the second surface of the device. As a result, the relative motion between the engager and the stopper slides the device off the engager, thereby releasing the device from the introducer.

The invention may be used with any of a number of otolaryngological devices. In some embodiments, the invention may be used to position devices to dilate, provide mechanical support, and/or stent the Eustachian tube at location closer to a nasopharynx than an eardrum, e.g., the torus tubarius orifice, which in turn, maintains patency of the Eustachian tube. In such cases, device may be via the nasal and/or oral passages and nasopharyngeal opening of the Eustachian tube and does not require incision of the eardrum, ear canal or entry into the middle ear. In any case, the invention may be used to position otolaryngological device elsewhere in vivo as well.

The introducer may be provided as a part of an otolaryngological kit. For example, the kit may include one or more otolaryngological devices as described above, an introducer as described above, and a container containing the one or more devices and the introducer. When the kit includes a plurality of devices, they may vary in size. Optionally, the kit may further comprise instructions for using the introducer and the one or more otolaryngological devices and/or a bender for bending the guide to desired shape.

To use the kit, a device may be selected therefrom and loaded onto the introducer. The introducer is then used to manipulate the loaded device in an otolaryngological cavity. Upon actuation of the release mechanism, the loaded device may be released from the introducer. The introducer may then be withdrawn.

An Exemplary Introducer and Device

As discussed above, the introducers of the invention are generally constructed for use with an otolaryngological device. Depending on the construction of the device, introducer construction may vary. For example, the introducer of the invention may be used to position the stents described in U.S. Pat. No. 7,833,282 to Mandpe (hereinafter the "Mandpe stents") in the torus tubarius of a human patient to achieve Eustachian tube patency. To provide some background with respect to the Mandpe stents, FIGS. 1-4 depict exemplary Mandpe stents in various views.

As shown in FIG. 1, the Mandpe stent 1 includes an insertable member 10 having a first exterior major surface 12 having a shape generally corresponding the cross sectional area of the torus tubarius opening for a Eustachian tube of an ordinary human patient. The stent has a width indicated by A, which corresponds to the widest dimension of the member's bottom end 3. As shown, the bottom portion of the stent exhibits a generally flanged geometry. The stent has a length indicated by B, which corresponds to the distance between the top end 2 and the bottom end 3 of the member 10.

FIG. 2 depicts the stent of FIG. 1 in side view. As shown in FIG. 2, the stent also has a second major exterior surface 14. Surfaces 12 and 14 are both planar, have a substantially identical shape, and are parallel to each other. The thickness of the stent is generally uniform and indicated by C, which represents the distance between surfaces 12 and 14.

As shown in FIGS. 1 and 2, a central ventilating hole 20 having a generally circular shape serves as a means for providing fluid communication between major surfaces 12 and 14. Hole 20 has a diameter D. The dotted lines of FIG. 2 represent side walls 22 of the hole 20 carried from FIG. 1 and serves to indicate the upper and lower extent of the central ventilation hole 20. As shown, the sidewalls 22 of hole 20 extends in a substantially perpendicular orientation relative to surfaces 12 and 14. Four optional protrusions 40 extend from first surface 12.

The overall geometry of the stent 1 in perspective view is represented in FIG. 3. As shown, the stent member 10 has a preinsertion triangular arched shaped structure with the central ventilating hole 20. The first surface 12 and the second surface (not shown) are connected by a peripheral surface 50, which generally encircle the stent 1.

FIG. 4 represents cross-sectional views of the stent along a-a and b-b lines in FIG. 1. As shown in FIG. 4, the peripheral surface 50 takes the form of a concave groove bounded by contoured lips 30. In some instances, contoured lips 30 start from one lateral aspect of stent 1 near its bottom 3, cross the top 2 and terminate at the corresponding opposing lateral aspect of the stent 1. The groove and lip construction may serve as a means for immobilizing the stent.

The stent may be made from any of a number of materials. Typically, the insertable member is formed in large part or entirely from a biocompatible and optionally resorbable material that is non-toxic, noninflammatory and nonimmunogenic. Suitable hydrophilic polymers used herein include polyethylene glycol, polyoxyethylene, polymethylene glycol, polytrimethylene glycols, polyvinylpyrrolidones, and derivatives thereof. Hydrophobic such as silicones, polyethylenes, polypropylenes, polystyrenes, may be used as well. The material is typically synthetic or man-made. However, a naturally occurring composition may be used as well. Biocompatibility typically requires a material purity of a pharmaceutically acceptable grade.

The stents of the invention may be used in conjunction with pharmaceutical technologies known in the art. For example, the stent may include a pharmacologically active constituent. Such constituents may be bound to the stent or may be eludable. Such pharmacologically active constituents may promote post-operative healing and may include, for example, antibiotics, antifungal agent, anti-inflammatory, or the like. In the alternative, the biocompatible material may be free from any pharmacologically active constituents.

Figures 6A, 6B:
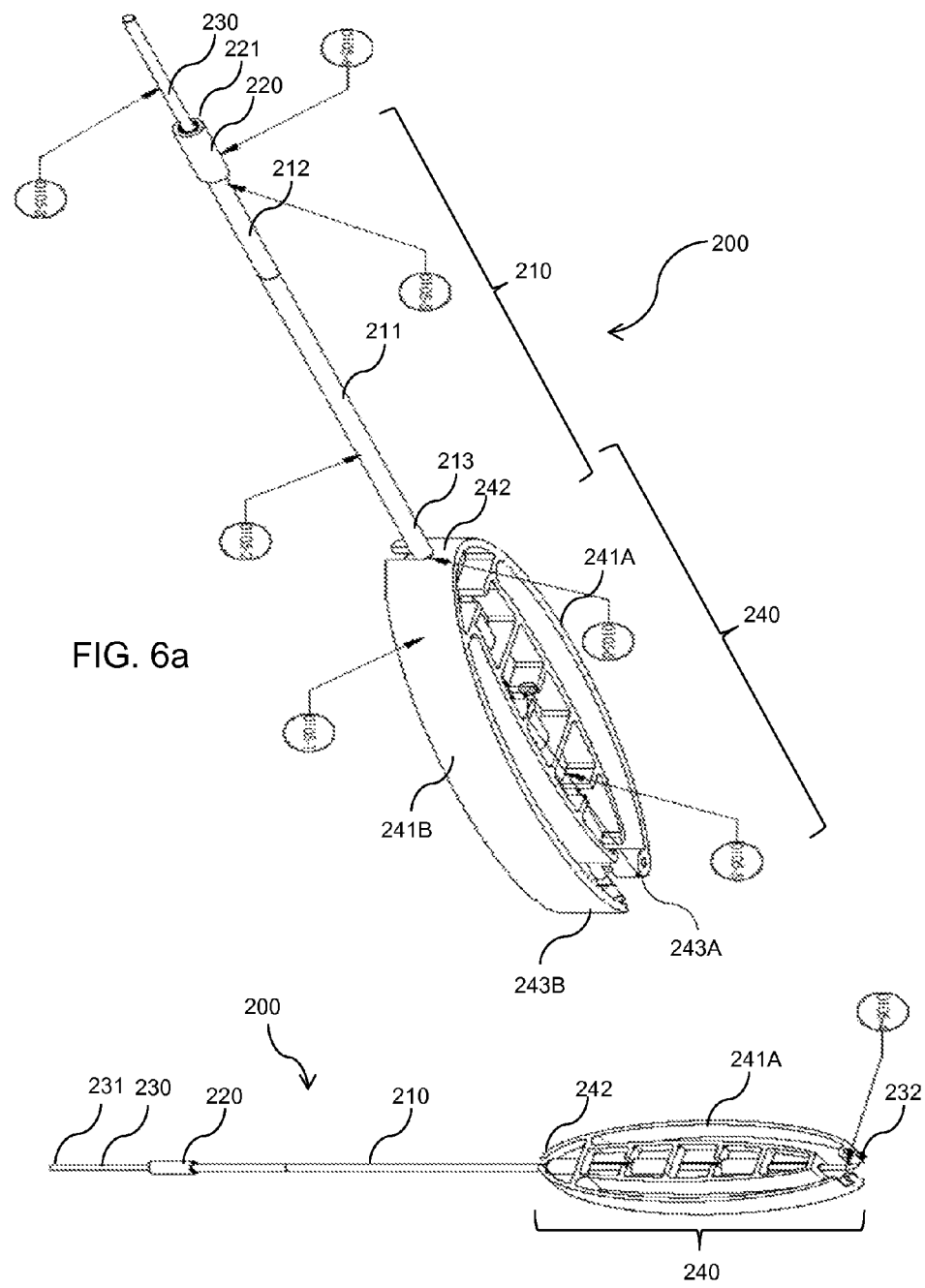
FIGS. 6a and 6b, collectively referred to as FIG. 6, shows perspective views of an exemplary introducer of the invention.

FIG. 6 shows an exemplary introducer of the invention that may be used with otolaryngological devices such as Mandpe stents. FIG. 7 shows how the introducer shown in FIG. 6 may be used with an otolaryngological device in the form of the Mandpe stent. As is the case with all figures referenced herein, in which like parts are referenced by like numerals, FIG. 7 is not necessarily to scale, and certain dimensions may be exaggerated for clarity of presentation.

The introducer should provide a user sufficient degree of control over the insertion and/or extraction of the device in a minimally invasive manner to minimize trauma or discomfort to a patient. As discussed in detail below, the introducer may be used to position the stent 1 into the torus tubarius through nasopharyngeal opening of the Eustachian tube. As shown in FIGS. 6 and 7, the introducer 200 includes a guide 210, a stopper 220 associated with the guide 210, an engager 230 coupled to the guide 210, and a release mechanism 240 attached to the engager 230. As shown, the guide 210 is provided in the form of an elongate tube 211 having a distal portion 212, a proximal portion 213, and a lumen 214 extending the length of the guide from a distal opening 215 to a proximal opening 216. As shown, the diameters of both the tube 211 and the lumen 214 are constant along the length of the guide. Accordingly, the tube wall thickness is substantially constant along the length of the guide as well.

Depending on the desired functionality of the introducer, the guide may be constructed from any of a number of materials. In some instances, the guide may be composed of a relatively stiff material such as stainless steel or titanium so that the guide may hold its shape for positioning the device during use. Alternatively, the guide may exhibit certain flexibility. In a preferred embodiment, the guide may be composed of a material or exhibit a construction that may be bent or otherwise deformed to a desired shaped before use that can hold its shape during use. Such materials may be polymeric and/or metallic in nature. In any case, the guide of the introducer may be formed from stock or off-the-shelf items, e.g., stainless steel tubing.

Also shown in FIGS. 6 and 7, the stopper 220 may take the form of a hollow cylinder compassing the guide 210 at a position closer to the distal portion 212 than the proximal portion 213 of the guide 210. More specifically, the stopper 220 is immobilized about the distal tip of the guide 210. The stopper 220 has a substantially planar surface 221 that faces away from the proximal portion 213 of the guide. In any case, the stopper may be formed from the same or different materials as the guide. Sometimes, the stopper may be formed from stock or off-the-shelf items as well. Alternatively (not shown), the stopper may be an integral part of the guide.

Figures 7A, 7B:
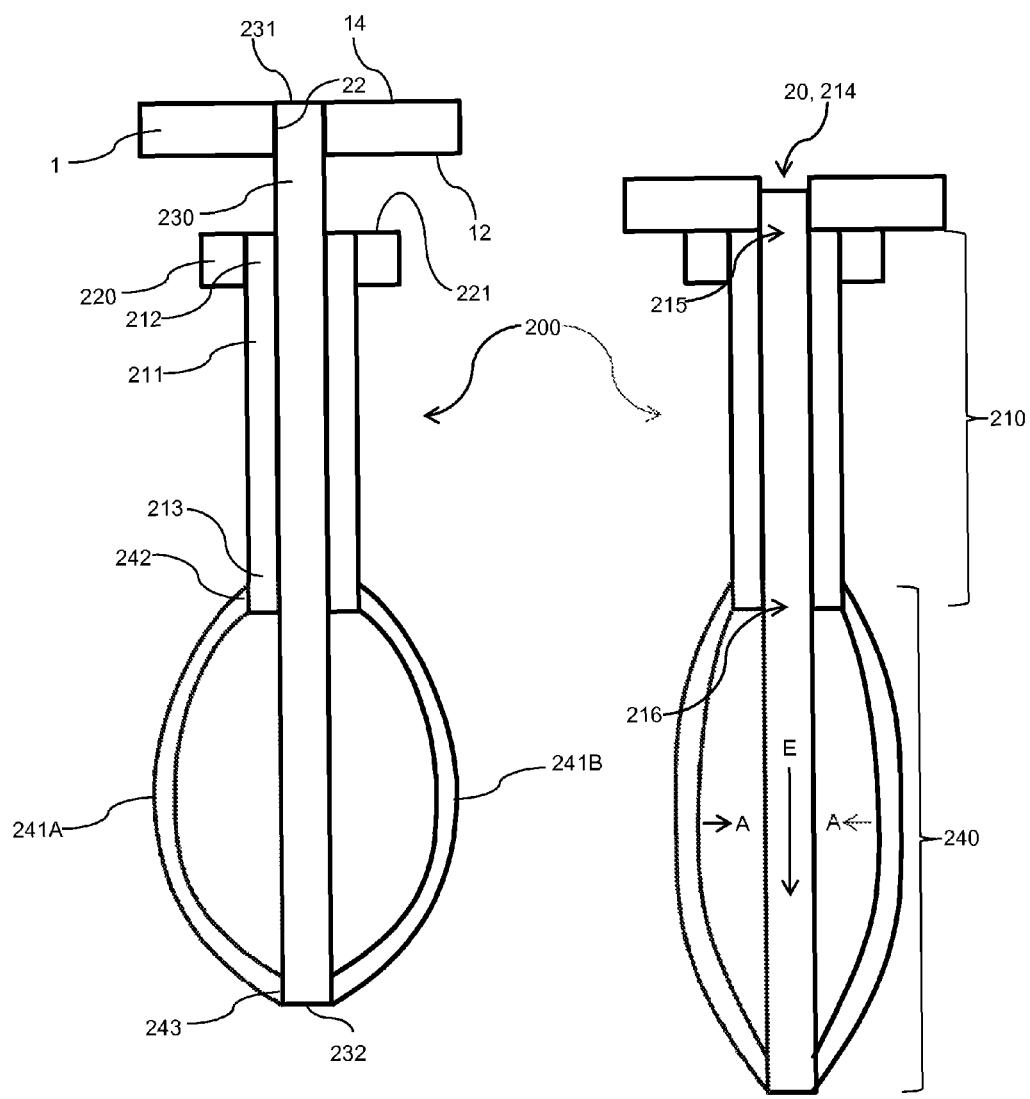
FIGS. 7a and 7b, collectively referred to as FIG. 7, show in cross sectional view how the introducer shown in FIG. 6 may be used with the device shown in FIG. 1-5 or other devices having a hole-type interface.

Further shown in FIGS. 6 and 7, the engager 230 coupled to the guide 210 may extend from a distal terminus 231 to a proximal terminus 232. While the bulk of the engager 230 is shown located within the lumen 214 of the guide 210, the engager 230 extends past stopper surface 221 and the proximal opening 216 such that both the distal and proximal termini of the engager lie outside the guide 210. As shown in FIG. 7A, the distal terminus 231 is located outside the guide 210 at an external position closer to the distal opening 215 than the proximal opening 216, whereas the proximal terminus 232 is located closer to the proximal than the distal opening.

As discussed above, the inventive introducer also includes a release mechanism 240 that may be positioned closer to the proximal portion of the guide 210 than the stopper 220. As shown in FIGS. 6 and 7, the release mechanism 240 may include a plurality of symmetrical bowed members. The bowed members 241 may come together at distal end 242, which may be immobilized to a proximal portion 213 of the guide 210. In addition, at least one of the bowed member 241 may be attached, directly or via one or more intermediary members, to the engager 230, to serve as an actuator. More specifically, at least one bowed member 241A may have a proximal end 243 attached to the proximal terminus 232 of the engager 230.

The release mechanism may be constructed in any of a number of ways. For example, one may assemble the release mechanism using components produced through injection molding or other techniques known in the art. Optionally, the release mechanism or portions may be contained a housing.

As discussed in detail below, the actuator 241A may be movable in an actuator motion effective to slide the distal terminus 231 of the engager 230 in an engager motion direction toward the guide 210. In some instances, the actuator motion direction may differ from the engager motion direction. For example, the actuator motion direction may be substantially perpendicular to the engager motion direction.

In any case, FIG. 7 shows that how the engager 230 may be slidable relative to the guide 210. To facilitate sliding motion, the engager is shown having a shape that generally does not exceed a critical dimension of the guide lumen 214. Thus, when the guide lumen 214 has a generally cylindrical shape, the engager 230 may take the form of an elongate cylinder having a diameter that does not exceed the diameter of the lumen. For example, the engager may consist essentially of an elongate and substantially cylindrical polymeric filament.

In general, the introducer should have a construction that allows the engager coupled thereto to slide relative to the guide without disturbing the shape of the guide, particularly when the guide has been adjusted to a desired shape (discussed below) and the engager fits snuggly within the guide. In some instances, the engager may be made more easily deformable than the guide. As a result, the shape of the guide is maintained while the engager is allowed to slide relative to the guide. Thus, the engager may be composed of a relatively flexible relative to the guide material. For example, when the guide is made from a metallic material, a less rigid metallic or polymeric material may be used to form the engager to allow the engager to slide within the lumen of the guide.

Also as shown in FIG. 7, the engager 230 may be frictionally engaged to the Mandpe stent 1. In particular, the distal terminus 231 of the engager 230 may be frictionally engaged with the sidewalls 22 of the central ventilating hole 20 of the stent. As the hole 20 may exhibit a generally circular cross-sectional area, the distal terminus 231 of the engager 230 may also exhibit a substantially circular cross-sectional area. In any case, the engager should be formed from a material that allows for its frictional engagement to any device useable with the inventive introducer. As discussed below in detail, once engaged to the engager via frictional forces, the device may be rendered immobile relative to the engager unless frictional forces are overcome.

Exemplary Operation of the Introducer and Device

As discussed above, the introducer of the invention has a simple yet effective construction for manipulating and positioning otolaryngological devices such as stents during medical and/or surgical procedures. Typically, an appropriate device is selected for insertion. After evaluating the location of the Eustachian tube orifice, the introducer may be bent appropriately with the bender. The device is loaded onto the introducer. Then, the introducer is manipulated to the device in an otolaryngological cavity. When the device is properly situated within the cavity, the release mechanism of the introducer is actuated. As a result, the device is released, and the introducer is withdrawn from the cavity.

As discussed in U.S. Pat. No. 7,833,282 to Mandpe, the stent 1, as illustrated in FIG. 5, may be inserted into an otolaryngological cavity, e.g., the torus tubarius 120 of a human patient to achieve Eustachian tube patency. FIG. 5 contains a cross-sectional representation of the ear along the external auditory canal and length of the Eustachian tube 90. The external ear or pinna 60 is the most lateral structure. The eardrum 70 and middle ear space 80 are not violated in the insertion process. The Eustachian tube orifice or torus tubarius 120 resides within the nasopharynx 100. When the stent 1 is properly positioned, the lips 30 and groove 50 allows the stent 1 to be snapped into the anterior and posterior lips of the torus tubarius 120.

Generally, the introducer may be used in a procedure that inserts the stent through a nostril or mouth of the animal into the Eustachian tube. For example, the introducer may insert the stent solely through the nasopharyngeal opening of the Eustachian tube through the nose or the oropharynx in a manner that does not involve making any incision to an eardrum or ear canal skin. The stent may then be released in a manner effective to allow the device to immobilize itself within the Eustachian tube at its opening in the nasopharynx. The procedure may be performed with local anesthesia or sedation as appropriate.

Once the stent has been properly positioned and immobilized, the Eustachian tube remains patent. During the device-induced patency of the Eustachian tube, the middle ear is aerated. The device effectively becomes a portal to drain fluid and infection from the middle ear.

Introducers of the invention are typically constructed for handheld operation. To allow a user operational access to regions of otolaryngological cavities of interest, the inventive introducer may have an overall length of approximately 10 to about 45 cm. Otolaryngological cavities of interest include, for example, oral and nasal cavities, paranasal sinuses, the upper trachea and esophagus, the Eustachian tube, the tympanic cavity and other regions of the ear, etc.

FIG. 7 depicts how the introducer 200 shown in FIG. 6 may be used with the stent 1, shown in FIG. 1-5 or with other devices having a hole-type interface. As shown in FIG. 7a, the Mandpe stent 1 is placed onto the engager 230 of introducer 200 such that surface 12 faces toward the engager's proximal terminus 232. That is, the distal terminus 231 of the introducer's engager 230 is placed through the central ventilating hole 20 of the insertable member 10. As alluded to above, the engager' distal terminus 231 has a cross section shape and area that allows the distal terminus 231 to be frictionally engaged to the sidewalls 22 of ventilating hole 20. As a result, frictional forces render the stent 1 immobile relative to the engager 230.

The relative positions of the engager 230 and the stent 1 may vary depending on the specific construction of the stent 1 and the engager. For example, if the distal terminus of the engager has a tapered geometry (not shown) and the central ventilating hole of the stent has a cylindrical shape, the stent may be moved toward the proximal end of the engager until the diameter of the engager is sufficiently large to immobilize the stent via frictional forces. Accordingly, the distal terminus may or may not extend past surface 14 of the stent. Optionally, as shown in FIG. 7a, the end surface of the distal terminus 231 is rendered coplanar to surface 14 of the Mandpe stent 1.

FIG. 7b shows how the release mechanism 240 may be actuated to release the stent from the engager. As discussed above, the release mechanism 240 includes symmetrical bowed members 241. A user may employ a pinching motion, as indicated by directional arrows A, to actuate the release mechanism 240, thereby moving the centers of bowed members 241 toward the engager. As a result, the bowed members 241 become less bowed.

Simultaneously, as shown in FIG. 7b, the distal ends 242 of the bowed members 241 are moved apart from their corresponding proximal ends 243. As discussed above, the distal ends 242 of the bowed members 241 are attached to the proximal portion 213 of the guide 210, and the proximal end 243 of bowed member 241A is attached to the proximal terminus 232 of the engager 230. As a result, the engager 230 is slid in an engager motion, as indicated by arrow E, relative to guide 210.

Likewise, the distal terminus 231 of the engager 230 is moved toward the guide 210. As surface 12 of stent 1 abuts surface 221 of the stopper 220 and the release mechanism 240 pulls the engager toward the guide 210, the frictional forces immobilizing the stent relative to the engager 230 is overcome. As a result, the device is unloaded or released from the introducer 200.

Kits and Accessories

To provide user convenience, streamline procedures, keep treatment rooms running efficiently, the invention provides an otolaryngological kit. The kit may include one or more otolaryngological devices, as described above, and an introducer as described above. Typically, the items are packaged within a container and may be accompanied with instructions for their use.

In some cases, the kit and items thereof may be disposable and/or constructed for single use. Alternatively, items in the kit may be reused. In any case, the introducer and/or one or more devices for use with the introducer are typically sealed within the container. Sterilization of the one or more devices and/or the introducer may occur before or after their placement in the container. The seal may help maintain the sterility of items within the container.

Typically, all devices of a kit have a substantially identical functionality. To accommodate the anatomic differences and needs of patients on which the kit may be used, however, devices of varying sizes may be used. For example, a kit may include a plurality of Eustachian tube stents of varying sizes for insertion into human patients of varying ages.

In use, a device may be selected from the kit. Typically, the device is selected for optimal fit according to the anatomical characteristics of the patient in need of the device. For example, a smaller device will be typically selected for introduction into an otolaryngological cavity of a child whereas a larger device may be selected for an adult. Alternatively, the device may be selected via trial and error. In any case, once the device is selected, it may be loaded onto the introducer. The introducer is then used to position the loaded device in the otolaryngological cavity. Once the release mechanism is actuated, the device is released from the introducer.

The inventive kit may also include a bender for bending the guide to a desired shape. Benders are useful to ensure that the guide exhibits a shape that minimizes trauma or discomfort to a patient when the introducer is introduced. Only on occasion may the guide be used without bending, since the otolaryngological cavities of interest may be accessed through relatively tortuous passageways via the nostrils or the mouth.

Figures 9A, 9B:
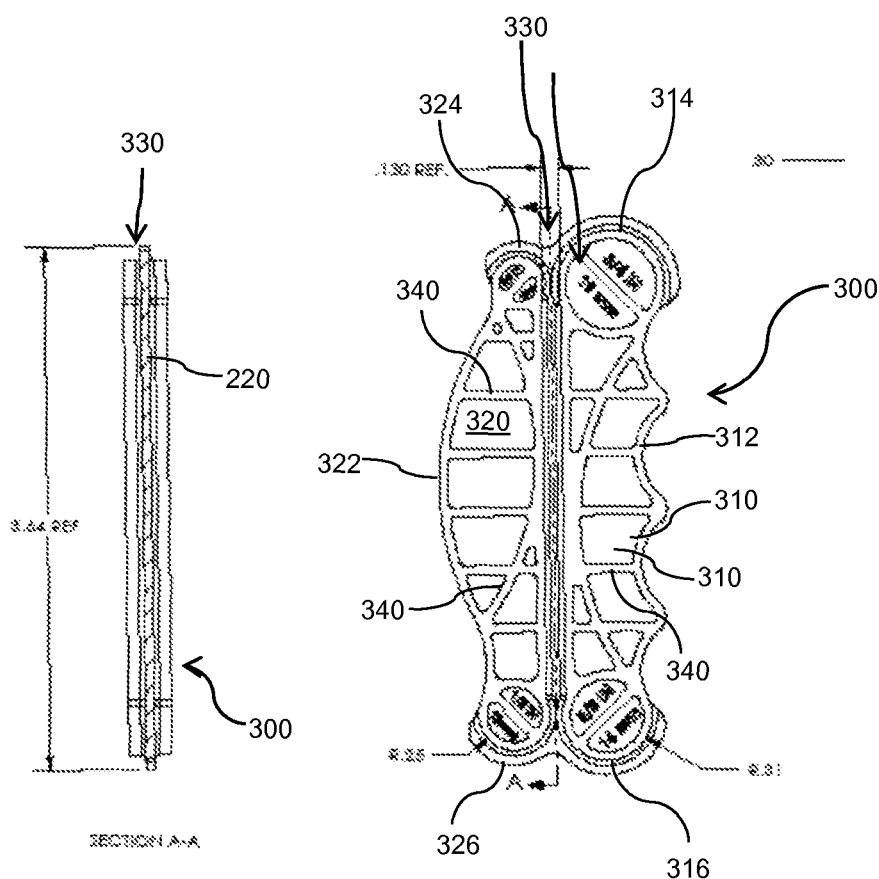
FIGS. 9a and 9b, collectively referred to as FIG. 9, depict an exemplary bender that may be used to shape the introducer shown in FIG. 6.

FIG. 9 depicts an exemplary handheld bender that may be used to shape the introducer shown in FIG. 6. As shown in FIG. 9a, the bender 300 includes first and second lateral regions, 310 and 320, respectively, and a trench 330 located therebetween. The trench 330, as shown in FIG. 9b, may be used to grip the guide 210 of the introducer 200. A number of supports 340 provides the bender 300 sufficient strength to withstand the stresses that the bender 300 may experience in operation.

The first lateral region 310 is bounded by a nubbed surface 312 that may serve as a conformal grip for human fingers. The nubbed surface 312 transitions into the ends of trench 330 via curved surfaces 314 and 316. Notably, surfaces 314 and 316 exhibit different radii of curvature. Similarly, the second region 320 is bounded by a convex surface 322 that may conform to the palm of a human hand. The convex surface 322 transitions into the ends of trench 330 via curved surfaces 324 and 326, which exhibit different radii of curvature from each other and from surface 314 and 316. In operation, a user may insert a portion of the guide into the trench and apply pressure to the lateral regions in order to hold the introducer in place while bending the guide may be bent to a desired shape against surface 314, 316, 324, and/or 326.

Miscellaneous Variations of the Present Invention

Variations on the construction of the inventive introducer will be apparent to those of ordinary skill in the art in view of the disclosure contained herein. For example, as discussed above, the introducer may be constructed such that the release mechanism may be actuated using an actuator motion that differs from the direction of engager motion. More specifically, as shown in FIG. 7b, the actuator motion direction is substantially perpendicular to the engager motion direction. However, different actuator and engager motion directions are not a requirement of the invention.

Figures 8A, 8B:
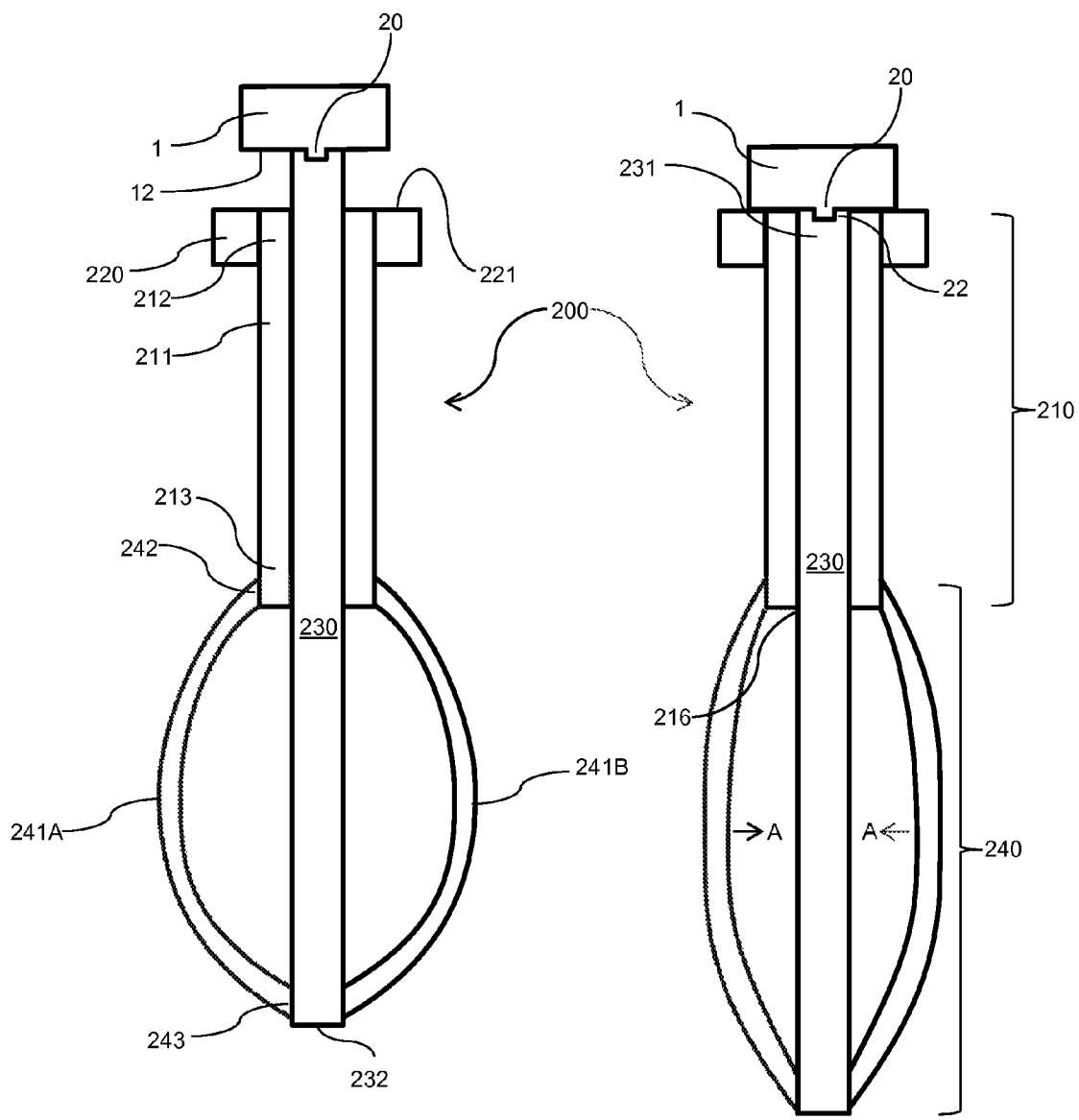
FIGS. 8a and 8b, collectively referred to as FIG. 8, show in cross sectional view how a device having a protrusion-type interface may be used with an introducer similar to that shown in FIG. 7, except with a modified engager.

As another example, FIG. 8 shows in cross sectional view how a device 1 having a protrusion-type interface 20 may be used with an introducer similar to that shown in FIG. 7, except with a modified engager 230. As shown, the device 1 is placed into the engager 230 of introducer 200 such that surface 12 faces toward the engager's proximal terminus 232. That is, the distal terminus 231 of the introducer's engager 230 is placed over the protrusion 20. As alluded to above, the engager's distal terminus 231 has a cross section shape and area that allows the distal terminus 231 to be frictionally engaged to the side walls 22 of the protrusion 20. As a result, frictional forces render the stent 1 immobile relative to the engager 230.

In any case, other variations of the present invention will be apparent to those of ordinary skill in the art in view of the disclosure contained herein. For example, while the invention has been described in detail for use with a living human patient, one of ordinary skill in the art may adapt the invention for use with nonhuman animals. Similarly, while the invention has been described in detail with respect to its functionality for introducing a stent into the Eustachian tube without substantially manipulating tissue near and/or of the Eustachian tube, the invention may be adapted to perform other functions as well. For example, the invention may be adapted for use for procedures in which a guide wire is threaded through the Eustachian tube into the middle ear or a balloon is used to dilate the Eustachian tube and/or orifice prior to placing the stent. Additional functionalities include, e.g., providing suction through the Eustachian tube for aspiration of the middle ear, delivering air or medications, performing endoscopic examination of the Eustachian tube and/or middle ear. It will be apparent to those of ordinary skill in the art that such additional functionalities may be carried out by through the use of introducers that are constructed for such purposes or through the use of other ENT equipment. In some instances, the introducer may be constructed to adjust the device to be inserted and/or extracted.

Other variations of the invention may be discovered upon engage in routine experimentation during the ordinary course of the practice of the invention. For example, the technologies described in Ockermann et al. (2010), "Balloon Dilation Eustachian Tuboplasty: A Feasibility Study," OTOLOGY & NEUROTOLOGY, 31:1100-03 and U.S. Patent Application Publication Nos. 20070244501, 20080154343, 20090163890, and 20100198191 can be employed with the invention.

It is to be understood that, while the invention has been described in conjunction with the preferred specific embodiments thereof, the foregoing description merely illustrates and does not limit the scope of the invention. Numerous alternatives and equivalents exist which do not depart from the invention set forth above. In general, any particular embodiment of the invention may be modified to include or exclude features of other embodiments. Other aspects, advantages, and modifications within the scope of the invention will be apparent to those skilled in the art to which the invention pertains.

All patents and patent applications mentioned herein are hereby incorporated by reference in their entireties to an extent not inconsistent with the disclosure provided above.

What is claimed is:

1. A medical or veterinary kit comprising:
a stent for insertion into a Eustachian tube of a human or an animal, the stent comprising a member having a preinsertion form that includes opposing exterior surfaces defining a member thickness therebetween, means for immobilizing the stent within the Eustachian tube, and means for providing fluid communication between the opposing surfaces through the member thickness to effect pressure equilibration therebetween, wherein at least one opposing surface defines a member length and member width, and the member length is greater than and perpendicular to the member thickness;
an introducer comprising a guide, an engager slidably coupled to the guide and constructed for engaging the stent such that frictional forces, unless overcome, immobilizes the stent relative to the engager, and a mechanism constructed to slide the engager relative to the guide and to overcome the frictional forces to position and release the stent within the Eustachian tube while the member remains in the preinsertion form; and
a medical or veterinary bender for shaping the guide of the introducer so that the guide may be shaped for introducing the stent into the Eustachian tube via a mouth and/or nostril of the human or animal rather than the human or animal's ear.

2. The kit of claim 1, wherein the opposing surfaces are connected by a peripheral surface that serves as the immobilizing means capable of engaging a surface of the Eustachian tube, thereby immobilizing the stent within the Eustachian tube when positioned by the introducer.

3. The kit of claim 1, wherein at least one of the exterior surfaces has a shape and size that corresponds to a triangular cross sectional area of the Eustachian tube.

4. The kit of claim 1, wherein the stent comprises a degradable biocompatible material.

5. The kit of claim 1, wherein the stent comprises a drug-eluting material.

6. The kit of claim 1, wherein the stent comprises a silicone material.

7. The kit of claim 1, wherein the opposing surfaces are planar.

8. The kit of claim 1, wherein the member width is greater than the member thickness.

9. The kit of claim 1, wherein the member length exceeds the member thickness by at least 50%.

10. The kit of claim 1, wherein the fluid communication providing means includes a hole extending through the opposing surfaces of the member.

11. The kit of claim 10, wherein the engager comprises an elongate and cylindrical filament having a distal terminus constructed for frictionally engagement to the hole of the stent member.

12. The kit of claim 11, wherein the guide is plastically deformable to a desired shape.

13. The kit of claim 11, wherein the guide comprises a tube having a lumen containing the engager.

14. The kit of claim 11, wherein the mechanism has an actuator that is movable in an actuator motion along an actuator motion direction, the actuator motion is effective to slide the distal terminus of the engager in an engager motion direction toward the guide, and the actuator motion direction differs from the engager motion direction.

15. The kit of claim 1, comprising a plurality of stents of varying sizes.

16. The kit of claim 1, without means for incising any ear drum or ear canal skin.

17. The kit of claim 1, wherein the member is formed at least in part from a biocompatible material that is degradable in the Eustachian tube at a predetermined degradation rate, and the immobilizing means is effective to immobilize the stent within the Eustachian tube for a predetermined period of time that corresponds to the predetermined degradation rate.

18. The kit of claim 17, wherein the predetermined period is about two to about eight weeks.

19. The kit of claim 18, wherein the immobilizing means is formed from the biocompatible material whose degradation ensures the stent being dislodged and completely extracted from the Eustachian tube after the predetermined period without surgical intervention.

20. The kit of claim 1, wherein the Eustachian tube includes a torus tubarius of a human child defined at least in part by anterior and posterior pillars meeting at a top portion of the torus tubarius, and the immobilizing means is adapted for positioning and immobilizing the stent at the torus tubarius.

21. The kit of claim 1, wherein the introducer interfaces the stent at a protrusion thereof.

22. The kit of claim 1, wherein the introducer interfaces the stent at an opening thereof.

23. The kit of claim 22, wherein the opening forms at least a portion of the means for providing fluid communication.

24. A medical or veterinary kit comprising:
- a stent for insertion into a Eustachian tube of a human or an animal, the stent comprising a member having a preinsertion form that includes opposing exterior surfaces defining a member thickness therebetween, means for immobilizing the stent within the Eustachian tube, and means for providing fluid communication between the opposing surfaces through the member thickness to effect pressure equilibration therebetween, wherein at least one opposing surface defines a member length and member width, and the member length is greater than and perpendicular to the member thickness;
- an introducer comprising bendable guide and a means for releasing the stent within the Eustachian tube while the member remains in the preinsertion form; and
- a medical or veterinary bender for shaping the guide of the introducer according to the physiology of the human or animal so that the stent may be inserted via a mouth or nostril of the human or animal into the Eustachian tube without need for incising a tympanic membrane.

* * * * *